United States Patent [19]
Dumoulin et al.

[11] Patent Number: 5,271,400
[45] Date of Patent: Dec. 21, 1993

[54] TRACKING SYSTEM TO MONITOR THE POSITION AND ORIENTATION OF A DEVICE USING MAGNETIC RESONANCE DETECTION OF A SAMPLE CONTAINED WITHIN THE DEVICE

[75] Inventors: Charles L. Dumoulin, Ballston Lake, N.Y.; Steven P. Souza, Williamstown, Mass.; Robert D. Darrow, Scotia, N.Y.

[73] Assignee: General Electric Company, Schenectady, N.Y.

[21] Appl. No.: 861,662

[22] Filed: Apr. 1, 1992

[51] Int. Cl.⁵ .............................................. A61B 5/055
[52] U.S. Cl. ................................. 128/653.2; 128/653; 128/658; 128/899
[58] Field of Search ............... 128/653.2, 653.5, 899, 128/658

[56] References Cited

U.S. PATENT DOCUMENTS

| | | | |
|---|---|---|---|
| 4,254,778 | 3/1981 | Clow et al. | 128/653.002 |
| 4,572,198 | 2/1986 | Codrington | 128/653.002 |
| 4,613,837 | 9/1986 | Blass et al. | 128/653.005 |
| 4,638,252 | 1/1987 | Bradshaw | 128/653.005 |
| 4,672,972 | 6/1987 | Berke | 128/653.005 |
| 4,799,015 | 1/1989 | Sepponen | 128/653.002 |
| 4,889,127 | 12/1989 | Takeda et al. | 128/653.002 |
| 4,962,763 | 10/1990 | Sato et al. | 128/653.002 |
| 4,966,149 | 10/1990 | Stokar | 128/653.002 |
| 4,989,608 | 2/1991 | Ratner | 128/653.002 |
| 4,995,394 | 2/1991 | Cline et al. | 128/653.002 |
| 5,005,592 | 4/1991 | Cartmell | 128/899 |
| 5,042,486 | 8/1991 | Pfeiler et al. | 128/653.001 |
| 5,099,845 | 3/1992 | Besz et al. | 128/899 |
| 5,107,862 | 4/1992 | Fabian et al. | 128/899 |
| 5,170,789 | 12/1992 | Narayan et al. | 128/653.5 |

FOREIGN PATENT DOCUMENTS

0385367 9/1990 European Pat. Off.
3937052 5/1990 Fed. Rep. of Germany.

Primary Examiner—Lee S. Cohen
Assistant Examiner—Brian L. Casler
Attorney, Agent, or Firm—Lawrence P. Zale; Marvin Snyder

[57] ABSTRACT

A tracking system employs magnetic resonance signals to monitor the position and orientation of a device, such as a catheter, within a subject. The device has an MR active sample and a receiver coil which is sensitive to magnetic resonance signals generated by the MR active sample. These signals are detected in the presence of magnetic field gradients and thus have frequencies which are substantially proportional to the location of the coil along the direction of the applied gradient. Signals are detected responsive to sequentially applied mutually orthogonal magnetic gradients to determine the device's position in several dimensions. The position of the device as determined by the tracking system is superimposed upon independently acquired medical diagnostic images. One or more devices can be simultaneously tracked.

16 Claims, 7 Drawing Sheets

TRACKING SYSTEM TO MONITOR THE POSITION AND ORIENTATION OF A DEVICE USING MAGNETIC RESONANCE DETECTION OF A SAMPLE CONTAINED WITHIN THE DEVICE

CROSS REFERENCES TO RELATED APPLICATIONS

This application is related to U.S. patent applications TRACKING SYSTEM TO MONITOR THE POSITION AND ORIENTATION OF A DEVICE USING MULTIPLEXED MAGNETIC RESONANCE DETECTION, Ser. No. 07/861,690 filed Apr. 1, 1992 and TRACKING SYSTEM AND PULSE SEQUENCES TO MONITOR THE POSITION AND ORIENTATION OF A DEVICE USING MAGNETIC RESONANCE, Ser. No. 07/861,718 filed Apr. 1, 1992 by Dr. Charles L. Dumoulin, Dr. Steven P. Souza and Robert Darrow all assigned to the present assignee, hereby incorporated by reference, and filed simultaneously with this application.

BACKGROUND OF THE INVENTION

1. Field of the Invention

The present invention relates to medical procedures in which a device is inserted into a body, and more particularly concerns tracking of such device with the use of magnetic resonance signals.

2. Description of Related Art

X-ray fluoroscopes are used routinely to monitor placement of devices during diagnostic and therapeutic medical procedures. Conventional X-ray fluoroscopes are designed to minimize X-ray dosage. Nevertheless, some procedures can be very long and the accumulated X-ray dose to the subject can become significant. The long term exposure of the attending medical staff is of even greater concern since they participate in these procedures regularly. Consequently, it is desirable to reduce or eliminate the X-ray dose during these procedures.

Another limitation on the use of X-ray fluoroscopes is that the technique is projective in nature and produces a single two-dimensional image. Information concerning the depth of an object within the field-of-view is not available to the operator. It is often desirable to obtain this information during surgical procedures.

Several methods of using rf signals to track a device in the body have been disclosed in U.S. patent applications TRACKING SYSTEM TO MONITOR THE POSITION AND ORIENTATION OF A DEVICE WITH RADIOFREQUENCY FIELD GRADIENTS Ser. No. 07/753,565 by C. Dumoulin, R. Darrow, J. Schenck and S. Souza; TRACKING SYSTEM TO MONITOR THE POSITION AND ORIENTATION OF A DEVICE WITH RADIOFREQUENCY FIELDS Ser. No. 07/753,563 by C. Dumoulin, R. Darrow, J. Schenck and P. Roemer; STEREOSCOPIC X-RAY FLUOROSCOPY SYSTEM USING RADIOFREQUENCY FIELDS Ser. No. 07/753,564 by C. Dumoulin and R. Darrow; AUTOMATIC GANTRY POSITIONING FOR IMAGING SYSTEMS Ser. No. 07/753,567 by C. Dumoulin and R. Darrow; and MULTI-PLANAR X-RAY FLUOROSCOPY SYSTEM USING RADIOFREQUENCY FIELDS Ser. No. 07/753,566 by R. Darrow and C. Dumoulin all filed on Sep. 3, 1991. These methods do not require the use of X-rays but employ rf transmitting and receiving apparatus to track a device in a body.

Currently, there is a need for a simple method of tracking a device in an imaging system which requires little modification to the existing system and does not require X-ray radiation for tracking.

SUMMARY OF THE INVENTION

Tracking of catheters and other devices being positioned within a body without using X-rays, is accomplished by using a magnetic resonance (MR) imaging system comprised of a magnet, pulsed magnetic field gradient system, a radio-frequency transmitter, a radio-frequency receiver and a controller. A device to be tracked is modified by attaching to it an MR active sample, such as water or a fluorinated hydrocarbon and a small radio-frequency (rf) coil near its end. A subject is placed in the magnet bore and the device is introduced into the subject. The MR system generates a series of rf and magnetic field gradient pulses which induce a resonant MR response signal from selected nuclear spins within the MR sample in the device. This response signal induces current in the rf coil attached to the device. Since the rf coil is small, its region of sensitivity is limited. Consequently, only nuclear spins in the immediate vicinity of the rf coil are detected by the rf coil. A receiver system receives the detected MR signal and demodulates, amplifies, filters and digitizes the signal which is then stored as data by a controller. Data are acquired during the sequential application of magnetic field gradients in three mutually orthogonal directions. These gradients cause the frequency of the detected signal to be directly proportional to the position of the MR active sample along each applied gradient. The digitized data are then processed using Fourier transformations to calculate the position of the MR active sample in three dimensions. This positional information can then be superimposed on an MR image of the region of interest.

In an alternate embodiment, instead of being attached to the device being tracked, the rf coil is an external coil which surrounds the subject and receives an MR response signal from the MR active sample affixed to the device.

OBJECTS OF THE INVENTION

It is an object of the present invention to provide a system for tracking a device within a body without using X-rays for tracking.

It is another object of the present invention to provide a method of tracking a device during an MR examination without loss of signal due to lack of MR active materials in the internal cavities of a subject.

It is another object of the present invention to provide an interactive image of a device superimposed upon another image.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawing in which:

DETAILED DESCRIPTION OF THE INVENTION

Figure 1:
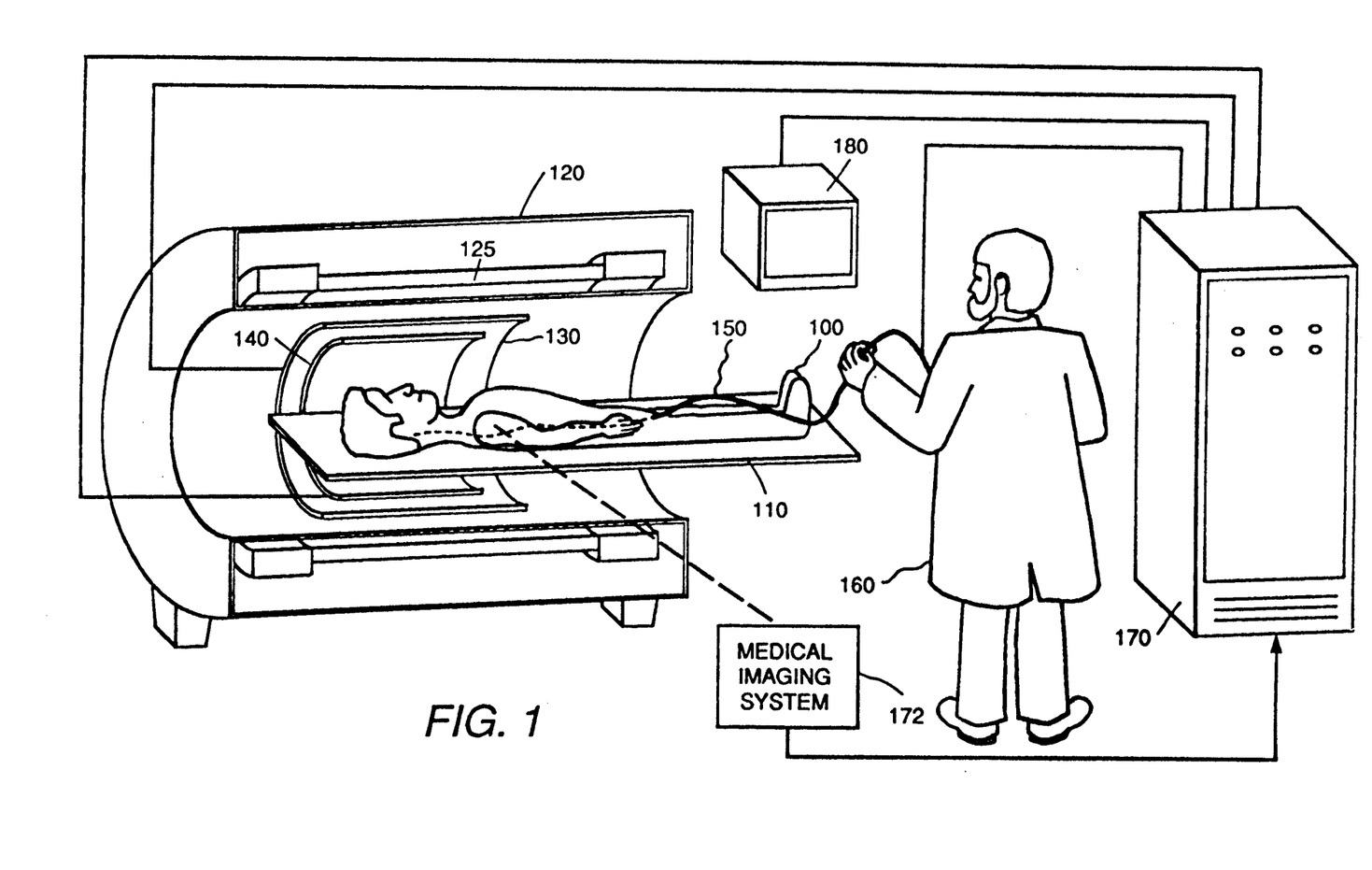
FIG. 1 is a perspective view of one embodiment of the present invention in operation tracking the location of a device in a subject.

In FIG. 1, a subject 100 on a support table 110 is placed in a homogeneous magnetic field generated by a magnet 125 in magnet housing 120. Magnet 125 and magnet housing 120 have cylindrical symmetry and is shown sectioned in half to reveal the position of subject 100. A region of subject 100 into which a device 150, shown as a catheter, is inserted, is located in the approximate center of the bore of magnet 125. An MR active sample, not visible in FIG. 1, is contained within device 150. Subject 100 is surrounded by a set of cylindrical magnetic field gradient coils 130 which create magnetic field gradients of predetermined strength at predetermined times. Gradient coils 130 generate magnetic field gradients in three mutually orthogonal directions.

An external coil 140 also surrounds the region of interest of subject 100. FIG. 1 shows one embodiment of a cylindrical external coil which has a diameter sufficient to encompass the entire subject. Other geometries, such as smaller cylinders specifically designed for imaging the head or an extremity can be used instead. Non-cylindrical external coils, such as surface coils may alternatively be used. External coil 140 radiates radio frequency energy into subject 100 and the MR active sample within device 150 at predetermined times and with sufficient power at a predetermined frequency to nutate nuclear magnetic spins of the MR active sample in a fashion well known to those skilled in the art. The nutation of the spins causes them to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

Device 150 is inserted into subject 100 by an operator 160. Device 150 may be a guide wire, a catheter, an endoscope, a laparoscope, a biopsy needle or similar device. This device contains an rf coil which detects MR signals generated in both the subject and the MR active sample within the device responsive to the radio frequency field created by external coil 140. Since the rf coil is small, the region of sensitivity is also small. Consequently, the detected signals have Larmor frequencies which arise only from the strength of the magnetic field in the immediate vicinity of the coil. These detected signals are sent to an imaging and tracking unit 170 where they are analyzed. The position of device 150 is determined in imaging and tracking unit 170 and is displayed on a display means 180. In the preferred embodiment of the invention, the position of device 150 is displayed on display means 180 by superposition of a graphic symbol on a conventional MR image driven by a superposition means as 174 in FIG. 6. In alternative embodiments of the invention, the graphic symbol representing device 150 is superimposed on diagnostic images obtained with other medical imaging systems shown as 172 in FIG. 1 such as a computed tomography (CT) scanner, a Positron Emission Tomography system or ultrasound scanner. Since CT scanners (and other X-ray imaging means), Positron Emission Tomography systems and Ultrasound scanners do not interfere with the steps of MR tracking, they may be operated during the steps of MR tracking. Alternatively, medical diagnostic images may be acquired with independent imaging means prior to initiating tracking and a symbol representing the location of the tracked device be superimposed on the previously acquired image. Other embodiments of the invention display the position of the device numerically or as a graphic symbol without reference to a diagnostic image.

Figures 2A, 2B:
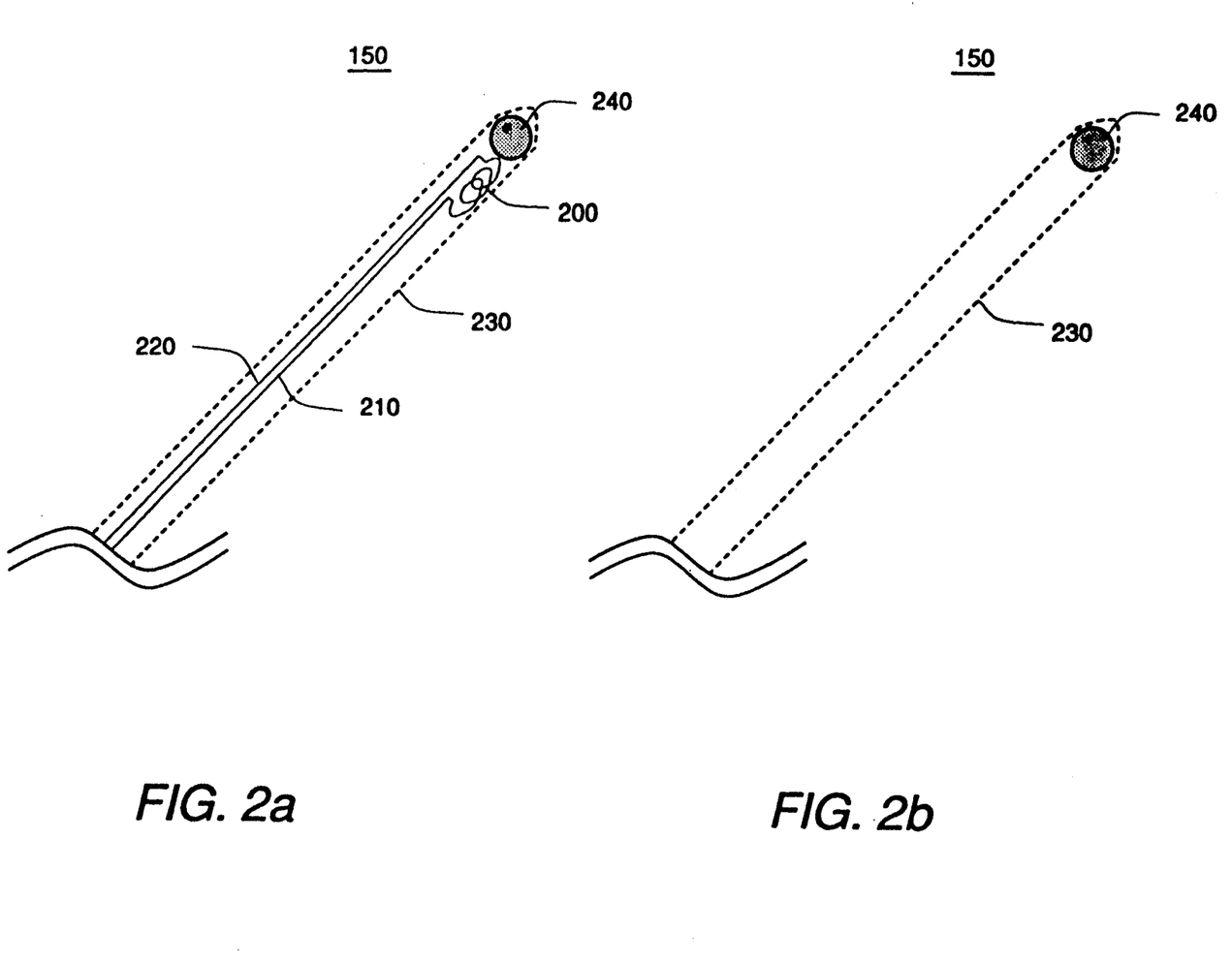
FIG. 2a is a schematic illustration showing an rf coil and an MR active sample incorporated into a medical device for insertion into the body of a subject.
FIG. 2b is a schematic illustration showing an MR active sample incorporated into a medical device for insertion into the body of a subject.

Two embodiments of device 150 are shown in detail in FIGS. 2a and 2b. In FIG. 2a, a small rf coil 200 is shown electrically coupled to the MR system via conductors 210 and 220. An MR active sample 240 is included in device 150. When MR active sample 240 experiences the proper magnetic field and rf excitation energy, it resonates at a specific frequency, emitting an MR response signal. The signal is sensed by rf coil 200 and passes through wires 210 and 220 to imaging and tracking unit 170 in the system of FIG. 1. In a preferred embodiment of this invention, conductors 210 and 220 of FIG. 2a form a coaxial pair and, together with rf coil 200, are encased in an outer shell 230 of device 150.

In an alternative embodiment, device 150 contains only MR active sample 240, as shown in FIG. 2b. When resonance of MR active sample 240 occurs, the signal emitted thereby is sensed by external coil 140 in the system of FIG. 1.

The embodiments of FIGS. 2a and 2b have the desirable feature that the MR response signal used to determine the position of device 150 is generated by MR active sample 240 and therefore the device is not required to be near an MR active region of the subject. An additional advantage of this embodiment is that artifacts arising from slight differences in the Larmor frequency of the detected spins caused by chemical shift phenomena can be avoided by using as the MR active sample a substance having a single MR resonance frequency. Furthermore, with this embodiment, a nuclear species not naturally found in the body (e.g. fluorine) may be used as the sample.

Figure 3:
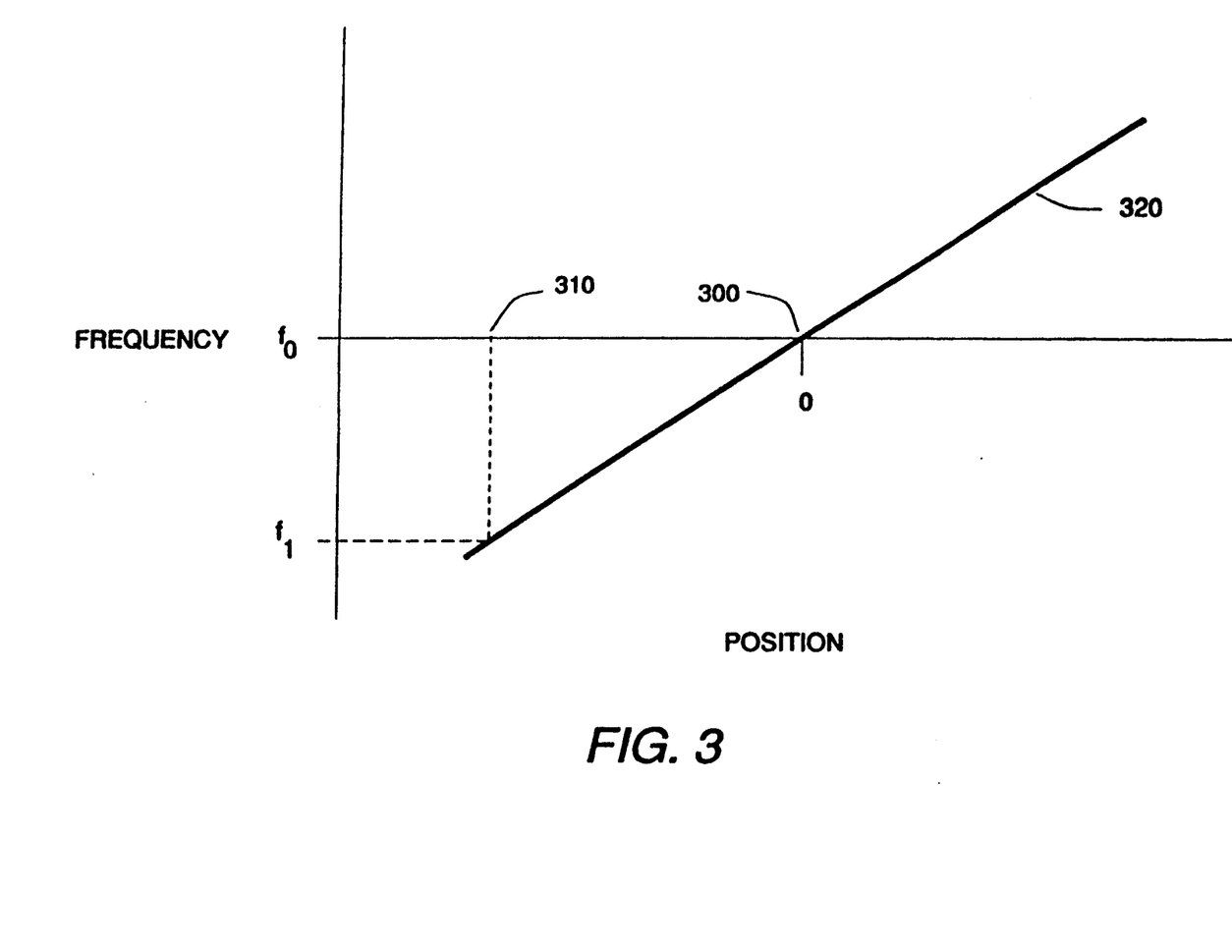
FIG. 3 is a graph of MR resonance frequency vs. position along a single axis in the presence of an applied magnetic field gradient.

Referring now to FIG. 3, the Larmor frequency of a spin is shown to be substantially proportional to its position when a magnetic field gradient is applied. A spin located at a center point 300 of gradient coil 130 (FIG. 1) precesses at a Larmor frequency $f_0$. The Larmor frequency $f_0$ at point 300 is determined solely by the static magnetic field generated by magnet 125 (FIG. 1). A spin at a location 310 has a Larmor frequency $f_1$ determined by the sum of the static magnetic field and the additional magnetic field created at that location by magnetic field gradient coil 130 (FIG. 1). Since the gradient coil response 320 is substantially linear, the Larmor frequency of the spin is substantially proportional to position.

Figure 4:
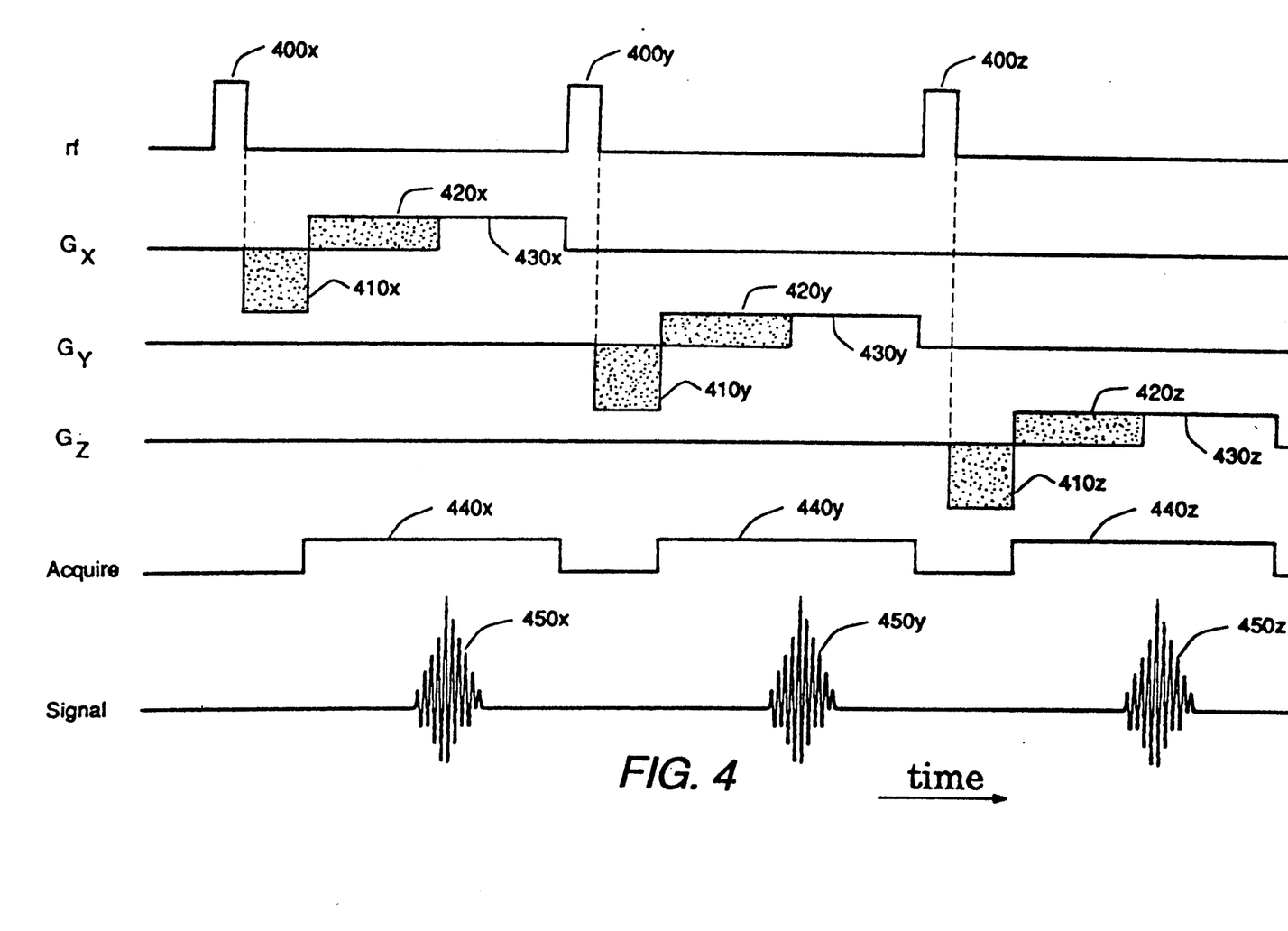
FIG. 4 is a timing diagram showing the relationships between rf pulses, magnetic field gradient pulses, data acquisition and detected signals in a first embodiment of the invention.

The MR response signal detected by rf coil 200 encased in device 150 as shown in FIG. 2 is generated in response to the rf and magnetic field gradient pulses of the MR system. A presently preferred embodiment of the pulse timing is illustrated in FIG. 4. In this timing diagram, a first broadband rf pulse 400x excites all spins of sample 240 within external coil 140 of FIG. 1. Shortly after first broadband rf pulse 400x, a first magnetic field gradient pulse 410x is applied in a predetermined direction. Gradient pulse 410x dephases spin magnetization to a degree proportional to the position of the spin along the applied field gradient (shown here to be in the X direction). Gradient pulse 410x is followed by a second magnetic field gradient pulse 420x having an opposite polarity to form a bi-lobed magnetic field gradient pulse. The product of the magnetic field gradient magnitude and duration of the gradient pulses (i.e., the areas of the regions shown in gray) are chosen to be substantially identical for the first and second gradient pulses. The amplitude of second magnetic field gradient pulse 420x, is maintained effectively creating a third pulse 430x having an area substantially identical to that of second pulse 420x. Note that second 420x and third 430x gradient pulses in fact form a single pulse. This single pulse has been divided in two pulses solely for purposes of identification. At the end of the second gradient pulse, all spins in sample 240 are substantially in phase. Third gradient pulse 430x causes additional dephasing of the MR signal.

During second gradient pulse 420x and third gradient pulse 430x, a data acquire signal 440x causes a first MR response signal 450x to be received by rf coil 200 (FIG. 2). MR response signal 450x is digitized and stored in imaging and tracking unit 170 (FIG. 1). MR response signal 450x has a maximum amplitude substantially at the end of second gradient pulse 420x and a Larmor frequency which is substantially proportional to the position of device 150 (FIG. 1) along the direction of the applied magnetic field gradient. The frequency of MR response signal 450x is used to measure the position of device 150 (FIG. 1) in a first direction which is parallel to the direction of the applied field gradient, $G_x$.

A second broadband rf pulse 400y is applied immediately after acquisition of first MR response signal 450x. In a manner analogous to that used to determine the position of device 150 of FIG. 1 in the first direction, a fourth, fifth and sixth gradient pulse 410y, 420y, 430y, respectively, are applied in a second direction (here indicated to be in the Y direction) substantially orthogonal to the first direction. A data acquire signal 440y is generated during the period of the fifth and sixth gradient pulses 420y, 430y to cause a second MR response signal 450y to be digitized and stored in imaging and tracking unit 170 of FIG. 1. After detection of MR response signal 450y, a third broadband rf pulse 400z is applied and a seventh, eighth and ninth gradient pulse 410z, 420z, 430z, respectively, are applied in a third direction (shown here to be in the Z direction) substantially orthogonal to the first and second directions. A data acquire signal 440z is generated during the period of the eighth and ninth gradient pulses to cause a third MR response signal 450z to be digitized and stored in imaging and tracking unit 170 of FIG. 1.

After detection of third MR response signal 450z, the entire pulse sequence shown in FIG. 4 is repeated until tracking of the device is no longer desired.

In another embodiment of this invention, the durations of third, sixth and ninth gradient pulses 430x, 430y, 430z, respectively, are extended to ensure that the signals are completely dephased before application of the next broadband rf pulse. This minimizes artifacts arising from spin phase coherence from multiple rf pulses. A second method of minimizing phase coherence is to use random phases in the MR system rf receiver and transmitter for each rf pulse.

In still another embodiment of this invention, the first fourth and seventh gradient pulses 410x, 410y, 410z, respectively, are reduced in amplitude and/or duration without changing the remaining gradient pulses. This reduces the amount of dephasing each signal experiences prior to the data acquisition period and thus shifts the instant of maximum signal, but not its frequency. Reducing the duration of the first, fourth and seventh gradient pulses 410x, 410y, 410z, respectively, permits an advantageous reduction in the rf pulse interval.

Figure 5:
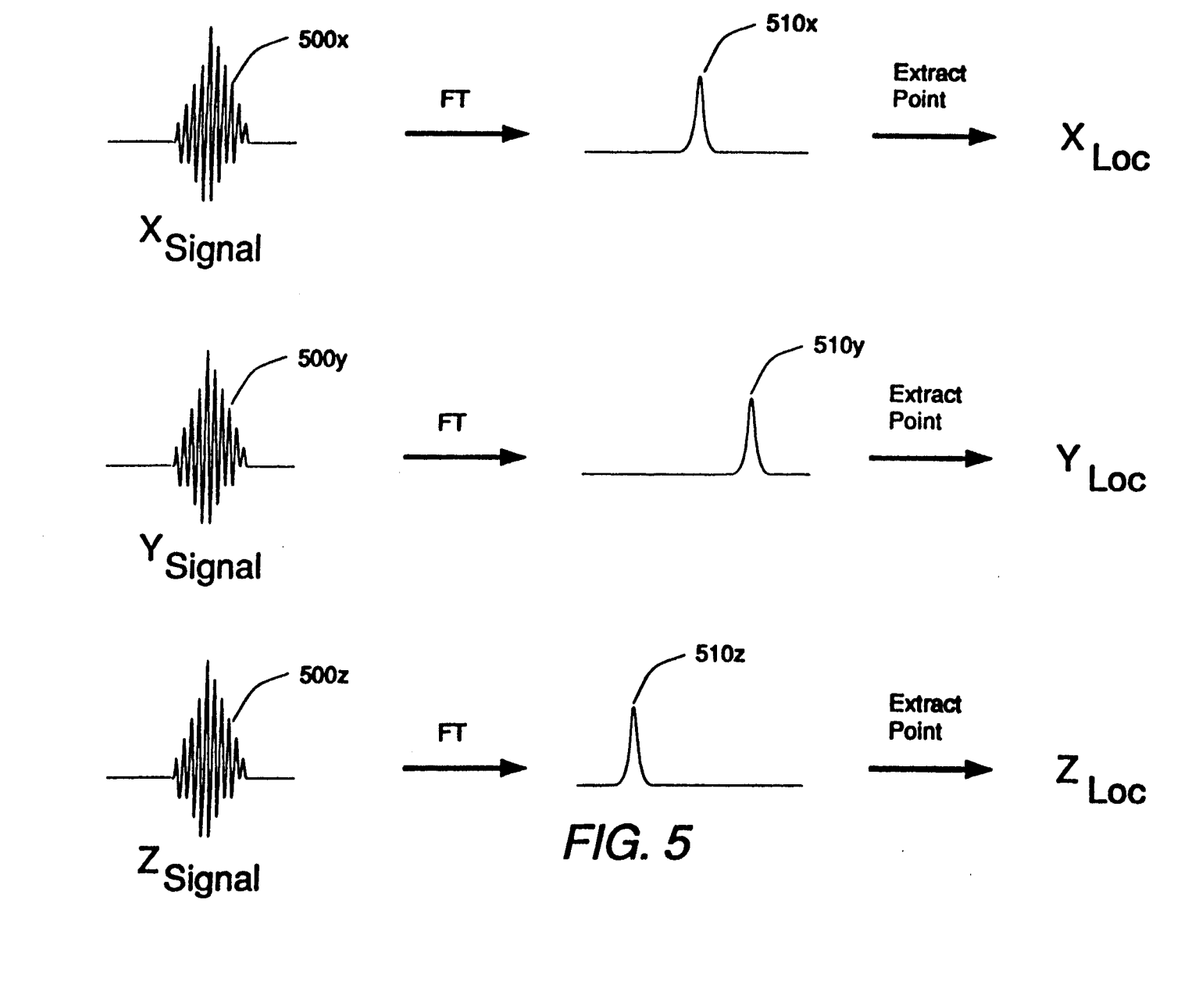
FIG. 5 is a diagram illustrating the steps required to determine the location of an MR active sample from an acquired MR response signal.

Referring now to FIG. 5, the steps executed by imaging and tracking unit 170 of FIG. 1 to determine the position of device 150 of FIG. 1 from the detected signals are illustrated. Three signals 500x, 500y, 500z are detected by the MR system responsive to the pulse sequence shown in FIG. 4. Signals 500x, 500y, 500z contain information about the position of the device in the X, Y and Z directions, respectively. This frequency information is extracted by subjecting each signal to a Fourier transformation (FT) which converts the time dependency of the data to frequency dependency. The frequency dependent data sets 510x, 510y, 510z each contain a single maximum which corresponds to position of the MR active sample in each of the three mutually orthogonal directions. The location of the maximum value in each data set is extracted and passed to display means 180 (FIG. 1) for presentation to the operator.

Figure 6:
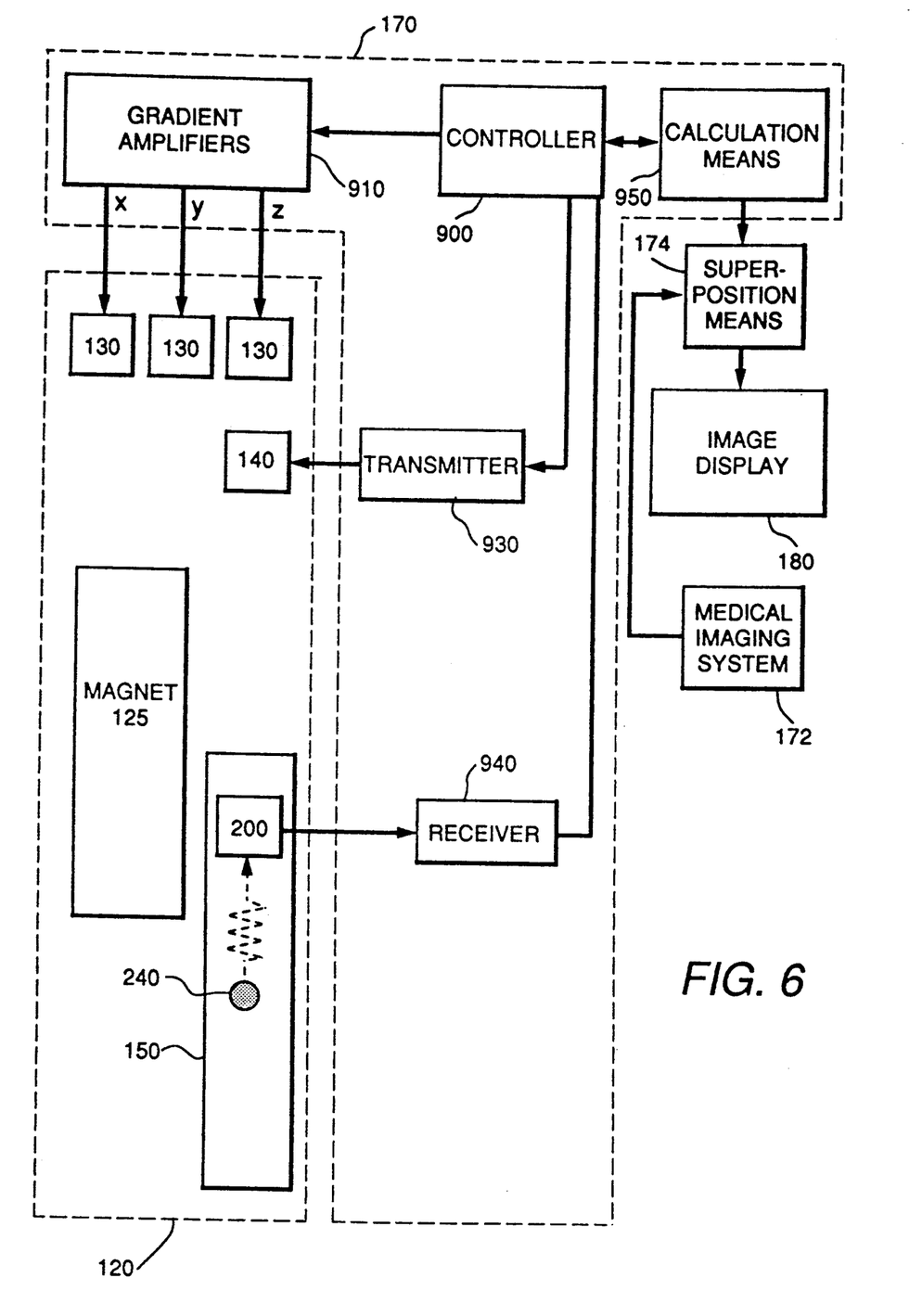
FIG. 6 is a block diagram of an MR imaging system suitable for device tracking using the present invention.

In FIG. 6, a block diagram of an MR system suitable for imaging and device tracking is illustrated. The system consists of a controller 900 which provides control signals to a set of magnetic field gradient amplifiers 910. These amplifiers drive magnetic field gradient coils 130 placed within the magnet 120. Gradient coils 130 are capable of generating magnetic field gradients in three mutually orthogonal directions. The controller 900 also generates signals which are sent to a transmitter means 930. These signals from controller 900 cause transmitter means 930 to generate rf pulses at a selected frequency and of suitable power to nutate selected spins within external coil 140 within magnet 125. An MR signal from MR active sample 240 is induced in rf coil 200 connected to a receiver means 940. Receiver means 940 processes the MR signal by amplifying, demodulating, filtering and digitizing it. The controller 900 also collects signals from receiver means 940. The signal from receiver means 940 is propagated to a calculation means 950 where it is processed. Calculation means 950 applies a Fourier transformation to the signal received from controller 900 to arrive at a position of MR active sample 240. The results calculated by calculation means 950 are displayed on an image display means 180.

In the preferred embodiments of the invention rf coil 200 placed within the device 150 performs a receive function. Reciprocity between the transmit and receive coils exists, however, and tracking systems in which rf coil 200 placed in device 150 is used to transmit rf energy, and external coil 140 is used to receive the MR response signal are possible.

Figure 7:
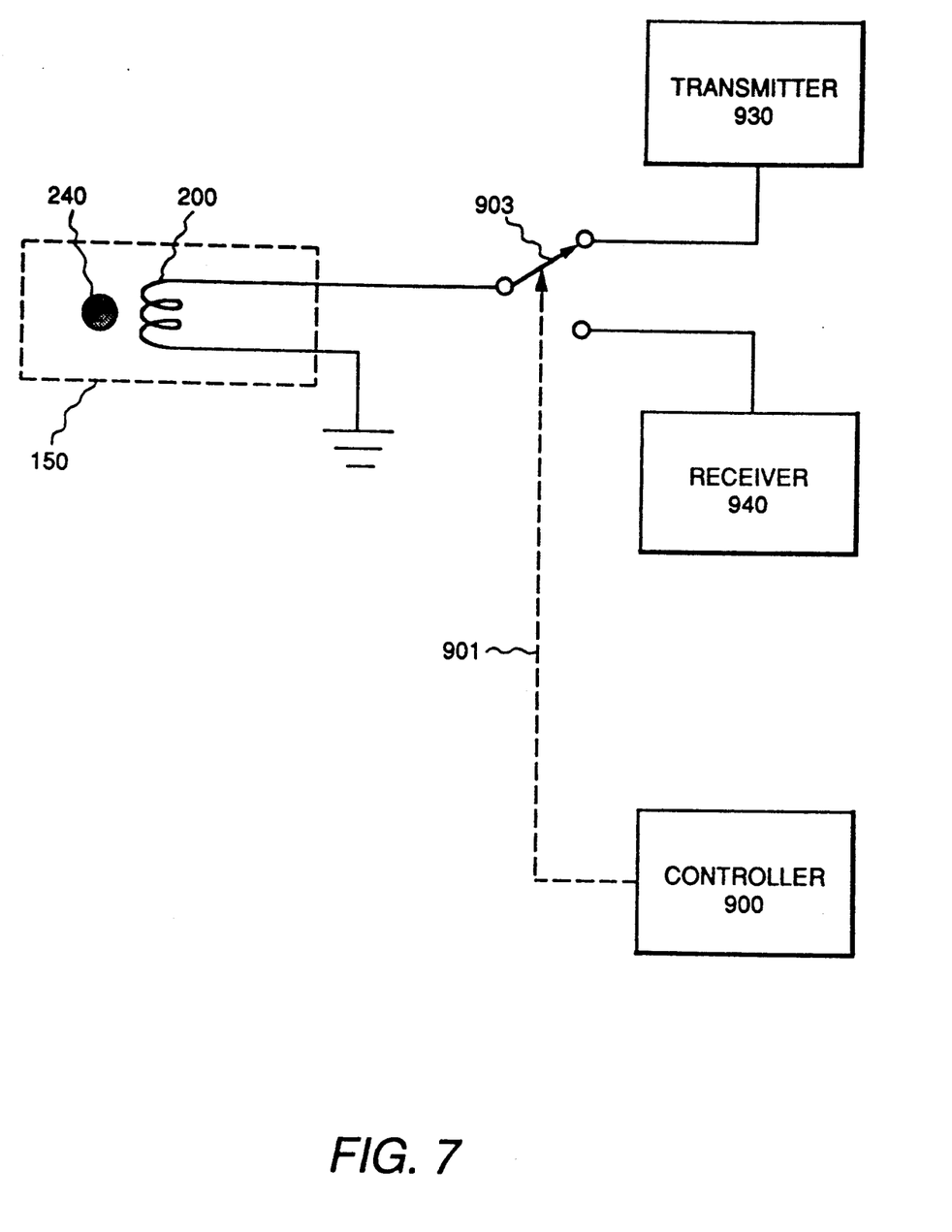
FIG. 7 is a partial block diagram of another embodiment of a tracking system according to the present invention.

In another embodiment of the invention, rf coil 200 may be used to alternately transmit and receive rf energy as shown in FIG. 7. Controller 900 activates a switch 903 through line 901 to connect coil 200 to transmitter 930 for transmitting RF energy into MR active sample 240 and the subject. Conversely, controller 900 activates a switch 903 to connect coil 200 to receiver 940 for receiving RF energy from MR active sample 240 and the subject.

In still another embodiment, external coil 140 may be used to alternately transmit and receive rf energy.

While several presently preferred embodiments of the novel MR tracking system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) tracking system comprising:
   a) an invasive device adapted to be inserted into a subject;
   b) an MR active sample incorporated into the invasive device;
   c) static magnetic field means adapted for applying a homogeneous magnetic field having substantially uniform amplitude over the subject;
   d) radiofrequency (rf) transmitter means adapted for transmitting rf energy of a selected duration, amplitude and frequency into the subject to cause nutation of a selected ensemble of spins within the subject and the MR active sample;
   e) gradient means for varying the amplitude of the magnetic field in at least one spatial dimension over the subject and the MR active sample over time causing the selected ensemble of spins to emit an MR response signal;
   f) detection means attached to the invasive device adapted for detecting an MR response signal from the selected ensemble of spins;
   g) calculation means adapted for calculating a location of the invasive device from the detected MR response signal;
   h) controller means coupled to the rf transmitter means, the detection means, the calculation means and the gradient means adapted for activating the rf transmitter means, the detection means, the calculation means and the gradient means according to a desired magnetic resonance sequence; and
   i) display means responsive to the calculation means adapted for displaying the location of the invasive device to an operator.

2. The MR tracking system recited in claim 1, wherein the MR active sample comprises a material which produces a measurable MR signal being other than a material that is commonly found in the subject.

3. The MR tracking system recited in claim 1 further comprising:
   a) imaging means for acquiring a medical diagnostic image of the subject; and
   b) superposition means for superimposing a symbol on the medical diagnostic image at a position representing the calculated location of the invasive device.

4. The MR tracking system recited in claim 3, wherein the imaging means for acquiring a medical diagnostic image is an X-ray imaging means.

5. The MR tracking system recited in claim 3, wherein the imaging means for acquiring a medical diagnostic image is an MR imaging means.

6. The MR tracking system recited in claim 3, wherein the imaging means for acquiring a medical diagnostic image is an Ultrasound imaging means.

7. The MR tracking system recited in claim 1, wherein the detection means comprises:
   a) an rf coil within the invasive device for receiving the MR response signal; and
   b) receiver means connected to the rf coil for processing the received MR response signal.

8. The MR tracking system recited in claim 1, wherein the invasive device is one of the group consisting of a guide wire, a catheter, an endoscope, a laparoscope and a biopsy needle.

9. The MR tracking system recited in claim 1, wherein the invasive device is a surgical device.

10. The MR tracking system recited in claim 1, wherein the invasive device is a therapeutic device.

11. A method for tracking a location of an invasive device within a subject employing magnetic resonance (MR) comprising the steps of:
    a) attaching a MR active sample to said invasive device;
    b) applying a homogeneous magnetic field having substantially uniform amplitude over said subject;
    c) transmitting radiofrequency (rf) energy of a selected duration, amplitude and frequency into the MR active sample and said subject to cause nutation of a selected ensemble of spins in said subject and the MR active sample;
    d) varying the amplitude of the magnetic field in at least one spatial dimension over time causing the ensemble of spins within the MR active sample to emit an MR response signal;
    e) detecting the emitted MR response signal from the MR active sample;
    f) processing the detected MR response signal;
    g) calculating a location of the MR active sample and said invasive device from the processed MR response signal; and
    h) displaying the location of said invasive device to an operator.

12. The method for tracking as recited in claim 11 further comprising the steps of:
    a) acquiring a medical diagnostic image of said subject; and
    b) superimposing a symbol on the medical diagnostic image at a position representing the calculated location of said invasive device.

13. The method for tracking as recited in claim 11, wherein the step of detecting the MR response signal occurs simultaneously with the step of varying the amplitude of the magnetic field.

14. The method for tracking as recited in claim 11, wherein the step of calculating a location of said invasive device further includes the step of performing a Fourier transformation on the MR response signal transforming time dependency to a frequency dependency, and converting the frequency dependency to a location of said invasive device.

15. A magnetic resonance (MR) tracking system comprising:

a) an invasive device adapted to be inserted into a subject;
b) an MR active sample incorporated into the invasive device;
c) static magnetic field means adapted for applying a homogeneous magnetic field having substantially uniform amplitude over the subject;
d) radiofrequency (rf) transmitter means attached to the invasive device adapted for transmitting rf energy of a selected duration, amplitude and frequency into the subject and the MR active sample to cause nutation of a selected ensemble of spins within the subject and the MR active sample;
e) gradient means adapted for varying the amplitude of the magnetic field in at least one spatial dimension over the subject and the MR active sample over time;
f) detection means adapted for detecting an MR response signal from the selected ensemble of spins;
g) calculation means adapted for calculating a location of the invasive device from the detected MR response signal;
h) controller connected to the rf transmitter means, the detection means, the calculation means and the gradient means adapted for activating the rf transmitter means, the detection means, the calculation means and the gradient means according to a desired MR sequence; and
i) display means connected to the calculation means adapted for displaying the location of the invasive device to an operator.

16. The MR tracking system recited in claim 15 wherein the detection means comprises an rf coil attached to the invasive device for receiving the MR response signal.

* * * * *